United States Patent
Niimi et al.

(10) Patent No.: US 11,926,845 B2
(45) Date of Patent: Mar. 12, 2024

(54) CELL CULTURE METHOD AND AUTOMATIC CELL CULTURE APPARATUS

(71) Applicant: Hitachi, Ltd., Tokyo (JP)

(72) Inventors: Yuki Niimi, Tokyo (JP); Hiroko Hanzawa, Tokyo (JP); Maiko Tanabe, Tokyo (JP); Kunio Ohyama, Tokyo (JP); Shizu Takeda, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 247 days.

(21) Appl. No.: 17/162,207

(22) Filed: Jan. 29, 2021

(65) Prior Publication Data

US 2021/0284959 A1 Sep. 16, 2021

(30) Foreign Application Priority Data

Mar. 11, 2020 (JP) ................................ 2020-041979

(51) Int. Cl.
*C12N 5/073* (2010.01)
*C12M 1/36* (2006.01)

(52) U.S. Cl.
CPC .......... *C12N 5/0605* (2013.01); *C12M 41/48* (2013.01); *C12N 2501/999* (2013.01); *C12N 2506/45* (2013.01); *C12N 2533/00* (2013.01); *C12N 2533/30* (2013.01); *C12N 2535/00* (2013.01)

(58) Field of Classification Search
CPC .......... C12N 5/0605; C12N 2501/999; C12N 2506/45; C12N 2533/00; C12N 2533/30
See application file for complete search history.

(56) References Cited

U.S. PATENT DOCUMENTS

2018/0195046 A1* 7/2018 Deng .................. A61K 35/545
2019/0085299 A1 3/2019 Tanabe et al.

FOREIGN PATENT DOCUMENTS

| JP | 2019-50773 A | 4/2019 |
|----|--------------|--------|
| WO | 2015005349 A1 | 3/2017 |
| WO | 2016143866 A1 | 8/2017 |

OTHER PUBLICATIONS

Okeyo, Kennedy O., et al. "Self-organization of human iPS cells into trophectoderm mimicking cysts induced by adhesion restriction using microstructured mesh scaffolds." Development, Growth & Differentiation 60.3: 183-194 (Year: 2018).*
Li, Zhuosi, Osamu Kurosawa, and Hiroo Iwata. "Establishment of human trophoblast stem cells from human induced pluripotent stem cell-derived cystic cells under micromesh culture." Stem cell research & therapy 10.1: 1-14. (Year: 2019).*
Sivasubramaiyan, K. et al., "Y-27632 enhances differentiation of blastocyst like cystic human embryoid bodies to endocrinologically active trophoblast cells on a biomimetic platform" Journal of Biomedical Science, Sep. 22, 2009, pp. 1-9, vol. 16, Issue 88 (9 pages).
Okeyo, K. et al. "Cell Adhesion Minimization by a Novel Mesh Culture Method Mechanically Directs Trophoblast Differentiation and Self-Assembly Organization of Human Pluripotent Stem Cells" Tissue Engineering: Part C, Jun. 3, 2015, pp. 1105-1115; vol. 21, No. 10 (11 pages).
Okeyo, K. et al. "Self-organization of human iPS cells into trophectoderm mimicking cysts induced by adhesion restriction using microstructured mesh scaffolds" Development, Growth, & Differentiation, Apr. 2, 2018, pp. 183-194 (12 pages).
Li, Z. et al., "Establishment of human trophoblast stem cells from human induced pluripotent stem cell-derived cystic cells under micromesh culture" Stem Cell Research & Therapy, 2019 (14 pages).
Notice of Reasons for Refusal received in corresponding Japanese Patent Application No. 2020-041979, dated Mar. 22, 2023, in 11 pages, with translation.

* cited by examiner

*Primary Examiner* — Arthur S Leonard
*Assistant Examiner* — Josephine M Gonzales
(74) *Attorney, Agent, or Firm* — Procopio, Cory, Hargreaves & Savitch LLP

(57) ABSTRACT

A novel cell culture method for inducing differentiation of a pluripotent stem cell into trophoblast and an automatic culture apparatus therefor includes: a first step of culturing the pluripotent stem cell in a presence of a ROCK inhibitor during a first time period; a second step of culturing the pluripotent stem cell, which has been subjected to the first step, without the ROCK inhibitor during a second time period following the first time period; and a step of culturing the pluripotent stem cell, which has been subjected to the second step, in the presence of the ROCK inhibitor during a third time period following the second time period, in which the pluripotent stem cell is cultured in a state of being adhered to a cell culture substrate including a planar mesh through the first to third time periods.

8 Claims, 5 Drawing Sheets

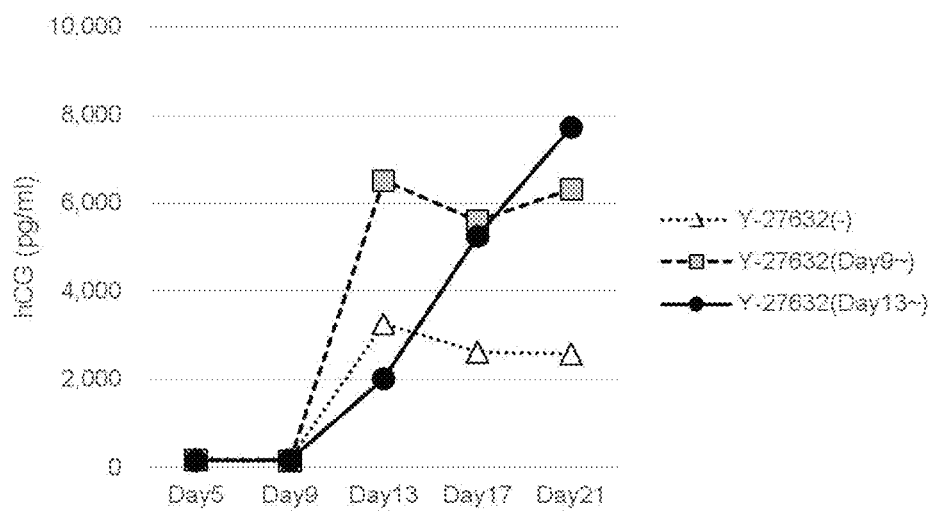
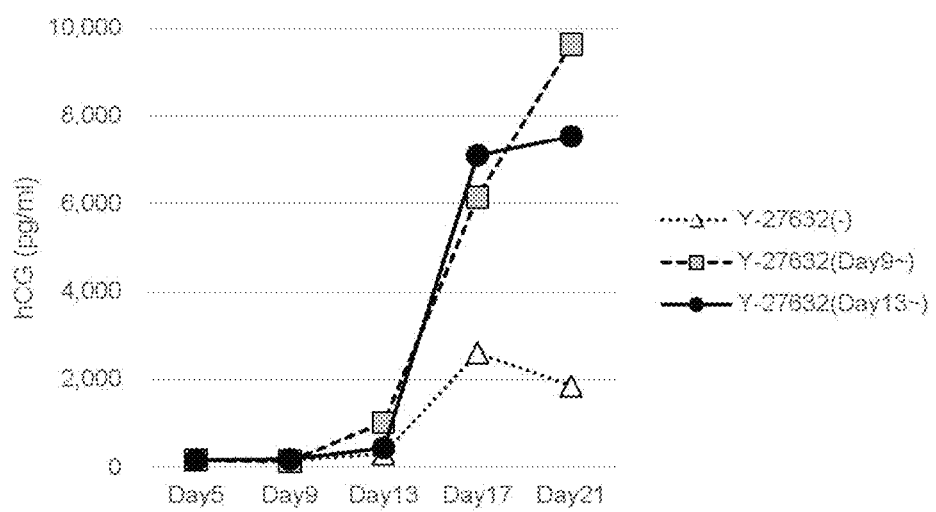

253G1 Parylene

253G1 Au

CELL CULTURE METHOD AND AUTOMATIC CELL CULTURE APPARATUS

BACKGROUND OF THE INVENTION

1. Field of the Invention

The present invention relates to a cell culture method and an automatic cell culture apparatus.

2. Description of the Related Art

In fetal development of mammals, a placenta is an essential organ that supplies nutrition and oxygen to a fetus. Although a placental tissue is mainly constituted by trophoblast, a developmental mechanism and a differentiation control mechanism are still unclear. A fact that the trophoblast can be easily produced not only has a potential to bring new knowledge to elucidation of human diseases caused by a placental abnormality that has been unknown until now, but can also be expected to be applied to industry such as development of in vitro test system for evaluating developmental toxicity.

Recently, a method of culturing human trophoblast stem cells (TS cells) in an undifferentiated state have been reported (WO 16/143866 (Patent Literature 1)). This report is groundbreaking in that human TS cells, which could not be cultured in an undifferentiated state, can be cultured for a long period of time with the ability to differentiate into a variety of placental tissues. However, because the establishment of TS cells requires human fetal placentas, the availability of donor placentas is limited. Although development of a method of inducing trophoblast from human pluripotent stem cells has been attempted so far, for example, in Kavitha Sivasubramaiyan et al., Journal of Biomedical Science, 2009 (Non Patent Literature 1), it is necessary to prepare an embryoid body from ES cells once, and it took a long time period of about 20 days to differentiate into the trophoblast.

On the other hand, a technique for culturing adherent cells including human iPS cells on a planar mesh has been developed (WO 15/005349 and JP-A-2019-50773 (Patent Literatures 2 and 3)). One of the features of this technology is that it does not require the passaging of adherent cells to maintain them. For culturing on a dish or plate, when cells become confluent, proliferation of the cells may stop, resulting in necrosis or gene mutation. Therefore, cell passaging with enzymatic treatment is required before reaching confluence. On the other hand, for the culturing using the planar mesh, cells are adhered to a mesh wire and proliferate, while dead cells generated during the culturing are desorbed to a lower side of the mesh, and thus can be removed at a time of medium replacement. Therefore, after cell seeding, only living cells can be cultured on the planar mesh for a long time period without cell passaging.

Further, it has been clarified that iPS cells autonomously differentiate into trophoblast by simply culturing the iPS cells on a planar mesh (Okeyo KO et al., Tissue Engineering Part C Methods, 2015, and Okeyo KO et al., Development, Growth & Differentiation, 2018 (Non-Patent Literatures 2 and 3)). It has been determined that, when iPS cells are seeded and cultured on a planar mesh, a part of the cells extending in a sheet shape along a mesh wire forms cysts above and below the sheet, and a trophoblast-specific protein is expressed in these cysts. On the other hand, it has been clarified that a phenomenon of differentiation into trophoblast depends on a strain of iPS cells and is a phenomenon observed only in a part of iPS cell strains (Zhuosi Li et al., Stem Cell Research & Therapy, 2019 (Non-Patent Literature 4)).

SUMMARY OF THE INVENTION

An object of the invention is to provide a novel cell culture method for inducing differentiation of a pluripotent stem cell into trophoblast and an automatic culture apparatus therefor.

One embodiment of the invention provides a cell culture method for inducing differentiation of a pluripotent stem cell into trophoblast, and the cell culture method includes: a first step of culturing the pluripotent stem cell in a presence of a ROCK inhibitor during a first time period; a second step of culturing the pluripotent stem cell, which has been subjected to the first step, without the ROCK inhibitor during a second time period following the first time period; and a step of culturing the pluripotent stem cell, which has been subjected to the second step, in the presence of the ROCK inhibitor during a third time period following the second time period, in which the pluripotent stem cell is cultured in a state of being adhered to a cell culture substrate including a planar mesh through the first to third time periods. The first time period may be a time period from a start of culturing to Day 1 after the start of culturing. The second time period may be a time period from Day 1 after the start of culturing to Day 7 to Day 15 after the start of culturing. The second time period may be a time period from Day 1 after the start of culturing to Day 9 to Day 13 after the start of culturing. The third time period may be a time period from Day 7 to Day 15 after the start of culturing to Day 11 or later after the start of culturing. The third time period may be a time period from Day 9 to Day 13 after the start of culturing to Day 13 to Day 21 after the start of culturing. The planar mesh may be coated with a film containing a metal, and the metal may be Au. The planar mesh may be coated with a biocompatible polymer, and the biocompatible polymer may be parylene.

Another embodiment of the invention provides an automatic cell culture apparatus by which any one of the cell culture methods described above is automatically performed. The automatic cell culture apparatus may include a cell observation mechanism.

A further embodiment of the invention provides a program for causing a computer to perform any one of the cell culture methods described above using an automatic cell culture apparatus. An embodiment of the invention also provides a computer-readable storage medium in which the program is stored.

According to the invention, it is possible to provide the novel cell culture method for inducing the differentiation of the pluripotent stem cell into trophoblast and the automatic culture apparatus therefor.

BRIEF DESCRIPTION OF THE DRAWINGS

FIG. 6 is a graph showing an amount of human chorionic gonadotropin (hCG) secreted into culture supernatant when a 201B7 strain is cultured on a rhombus mesh treated with parylene coating in a second example of the invention.

FIG. 7 is a graph showing an amount of hCG secreted into the culture supernatant when the 201B7 strain is cultured on the rhombus mesh treated with Au coating in the second example of the invention.

DESCRIPTION OF EMBODIMENTS

An embodiment of the invention will be described in detail below with reference to the figures, the objects, features, advantages, and ideas of the invention will be apparent to those skilled in the art from the description herein, and those skilled in the art can still easily reproduce the invention from the description of this specification. The embodiment and specific examples of the invention described below are preferred embodiments of the invention, are presented for purposes of illustration or description, and are not intended to limit the invention. It will be apparent to those skilled in the art that various changes and modifications can be made based on the description herein within the spirit and scope of the invention disclosed herein.

1. Planar Mesh

Figure 2A:
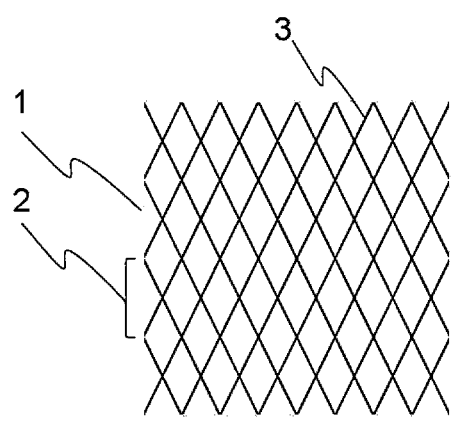
FIGS. 2A and 2B are a top view and a cross-sectional view of a cell culture substrate according to the embodiment of the invention.
Figure 2B:
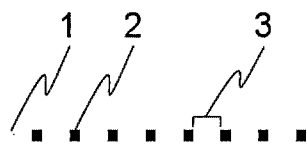

A cell culture substrate used in an embodiment of the invention will be described. The cell culture substrate has a planar mesh 1 structure, and openings 3 of the mesh each have an area through which at least one cell can pass. FIGS. 2A and 2B show a top view and a cross-sectional view of the cell culture substrate according to the embodiment of the invention.

Instead of cells adhering to and proliferating on a scaffold having a larger area than that of the cell or a scaffold having a smaller void area than the area of the cell as in a cell culture substrate of related art, when the cell culture substrate of the invention is placed in a medium, cells spontaneously extend to the openings 3 of the planar mesh 1 having an area larger than that of the cell while the cells adhere to the cell culture substrate. Thereafter, the cells proliferate on the cell culture substrate, and the openings 3 are covered with a plurality of cells. The cell culture substrate may be placed in a culture container in a state of being suspended in the medium. Further, a material for producing the cell culture substrate of the invention is not particularly limited, but preferably includes or be a metal that does not exhibit cytotoxicity and has high strength, such as pure nickel, titanium, platinum, Au, tungsten, rhenium, palladium, rhodium, ruthenium, and an alloy (stainless steel, titanium and nickel, nitinol, cobalt chrome, a non-ferrous alloy, and a platinum iridium alloy). If the strength is sufficient, for example, a photocurable resin, a biocompatible material, a biodegradable material may also be included. Examples of the photocurable resin include, but are not limited to, an acrylate compound, a methacrylate compound, an epoxy compound, an isocyanate compound, a thiol compound, and a silicon compound, and specific examples thereof include urethane acrylate, polyester acrylate, epoxy acrylate, poly(meth)acrylate, ethoxylated bisphenol A acrylate, aliphatic urethane acrylate, polyester acrylate, polyethylene terephthalate, polystyrene, polycarbonate, acrylic modified alicyclic epoxide, bifunctional alcohol ether type epoxide, acrylic silicon, and acrylic dimethyl siloxane. A material for the substrate preferably includes or is formed of the biocompatible material or the biodegradable material in that the material can be suitably used for regenerative medicine such as transplanting the cell culture substrate into a living body as it is. Examples of the biocompatible material include, but are not limited to, silicon, polyether block amide (PEBAX), polyurethane, silicone polyurethane copolymer, ceramics, collagen, hydroxyapatite, nylon, polyethylene terephthalate, ultra high molecular weight polyethylene such as Gore-Tex (registered trademark), polyvinyl chloride, and other bio-derived materials. Examples of the biodegradable material include, but are not limited to, polylactide (PLA), polyglycolide (PGA), polycaprolactone (PCL), a copolymer of polylactide (PLA), polyglycolide (PGA) and polycaprolactone (PCL), a natural polymer such as PHB-PHV poly (alkanoic acid)s, polyesters, starch, cellulose, chitosan and a derivative of natural polymer.

The planar mesh 1 can be appropriately prepared by a method known to those skilled in the art or a method based thereon according to a structure, application, or the like by using the above material, but is preferably the planar mesh 1 formed of a thin-line substrate. For example, when pure nickel or titanium is used, the planar mesh 1 can be prepared by an electroforming method, and when the photocurable resin is used, the planar mesh 1 can be prepared by a photolithography method. When the material for the cell culture substrate has cytotoxic or is other than the biocompatible material, a surface of a mesh wire 2 may be treated with the biocompatible material or the like.

A wire diameter of the mesh wire 2 is not particularly limited and can be appropriately determined by those skilled in the art in accordance with a material and a size of a cell to be cultured. In the cell culture substrate of the related art, a structure having a width equal to or larger than a maximum diameter of a cell is used so that the cells can be settled, whereas a wire diameter of the planar mesh 1-shaped substrate of the invention may be smaller than the maximum diameter of cells, may be 1 μm to 10 μm, and may be 1 μm or less. Here, the maximum diameter of the cells refers to a length of a longest straight line connecting two points around the cell.

A shape of the opening 3 of the planar mesh 1 is not particularly limited, and is typically a regular polygonal shape such as an equilateral triangle, a square, or a regular hexagon, but may be a circle or an ellipse in addition to a polygon such as a rhombus. The shape and a length of one side of the opening 3 are not particularly limited, but, for example, in a case of a rhombus, the length of one side of the opening 3 is preferably about 30 μm to 200 μm, and more preferably about 100 μm. In addition, the openings 3 may not all have the same shape, maybe a planar structure in which a plurality of openings 3 are set as one set, and each set is repeatedly arranged regularly or irregularly. The shape of the openings 3 may be random, or all the openings 3 may have different shapes.

It is preferable that the opening 3 has a size of one or more cells to be cultured, that is, a size that allows the cells to pass through the opening 3. In this case, the opening 3 may have a size that allows the cells to pass without coming into contact with the opening 3 or without deforming even when coming into contact with the thin-line substrate, and may have a size that allows the cells to pass while deforming due to coming into contact with the opening 3. A specific area of the opening 3 is not particularly limited, but is preferably 50 $\mu m^2$ or more.

In a case where a smallest diameter of the openings 3 is larger than the maximum diameter of the cells, when a mesh on a plane is placed horizontally and the cells are seed from above, some cells are settled on the mesh wire 2 and some cells fall down without coming into contact with the mesh wire 2. Initially, the openings 3 are not initially covered with only the cells settled on the mesh wire 2, but as the cells spontaneously extend toward a center of the opening, the openings 3 are covered with the cells.

2. Coating of Planar Mesh

In the planar mesh 1, coating with a metal also makes it possible to improve damage and a cell adhesion surface. Any metal can be used as the metal used herein as long as the metal has no cytotoxicity and has corrosion resistance to acids such as lactic acid, which is a cell metabolite. Au is exemplified as the metal, but the metal is not limited thereto.

Similar to the coating with a metal, by coating with a monomer, polymer or a mixture thereof (hereinafter, referred to as a monomer/polymer including these three), the damage due to corrosion of the mesh wire 2 and the cell adhesion surface can be improved. Any monomer/polymer can be used as the monomer/polymer used herein as long as the monomer/polymer has no cytotoxicity and is biocompatible. Examples of the monomer/polymer include: an acrylic resin (methyl acrylate, methyl methacrylate, 2-hydroxyethyl methacrylate, 2-hydroxyethyl acrylate, acrylic acid, methacrylic acid, glyceryl acrylate, glyceryl, glyceryl methacrylate, methacrylamide, acrylamide), vinyl (ethylene, propylene, chloroethylene, vinyl acetate, vinylpyrrolidone, vinylidene fluoride), nylon (polycaprolactam, polylauryllactam, polyhexamethylene biguanide, adipoamide, polyhexamethylene dodecane diamine), polyurethane, polycarbonate, polyamide, polysulfone, polyethylene terephthalate, dimethyl polysiloxane, polyether ketone, a perfluoroalkoxy fluororesin (Teflon (registered trademark), NEOFLON (registered trademark); polychlorotrifluoroethylene), a fluoroethylene propylene polymer (tetrafluoroethylene, hexafluoropropene), and expanded polytetrafluoroethylene, but a p-xylene resin is preferable, poly p-xylene is more preferable, and parylene is further preferable.

A coating method is not particularly limited, and an optimum coating method may be used for each metal and monomer/polymer, such as vapor deposition. A thickness of the coating may be such that the wire diameter of the thin-line substrate does not exceed a maximum cross-sectional length of the cells.

3. Cell Culture Substrate

Figure 3A:
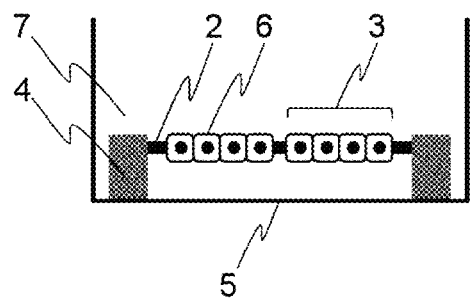
FIGS. 3A and 3B are cross-sectional views of a cell culture container according to the embodiment of the invention.
Figure 3B:
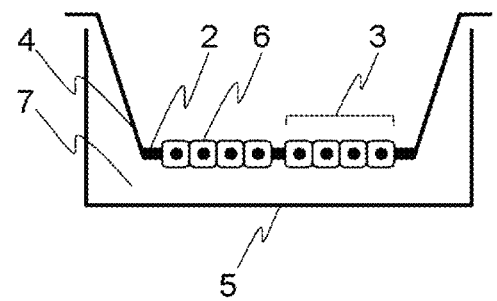

The planar mesh 1 may reinforce surroundings, which facilitates operations such as moving and shaping the cells in addition to culturing the cells. Examples of a method of reinforcing the planar mesh include, but are not limited to, a method in which a Kapton tape is attached to the surroundings and is fixed to a silicon plate to form a holding portion 4, a method in which a bottom surface portion of a cell culture insert is replaced with a mesh on a plane to form the holding portion 4. FIGS. 3A and 3B show examples of a cross-sectional view of the cell culture container of the invention in a state where the cells are being cultured.

It is preferable that the cell culture substrate including the planar mesh 1 is sterilized prior to a step of seeding the cells. A sterilization method can be appropriately selected by those skilled in the art.

4. Cell Culture Method

Figure 1:
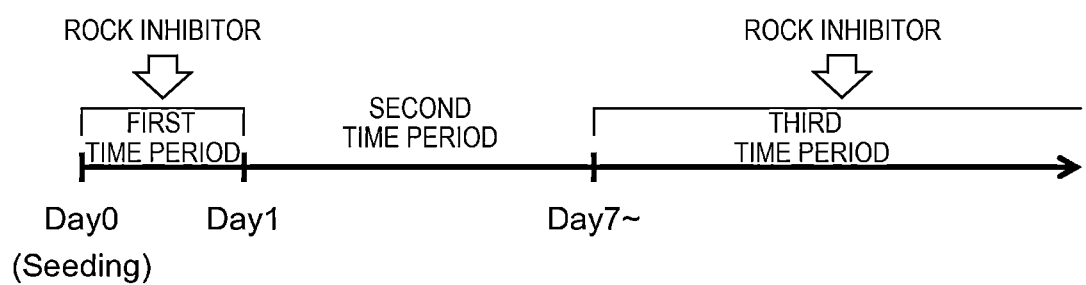
FIG. 1 is a diagram schematically showing a method of culturing pluripotent stem cells according to an embodiment of the invention.

A cell culture method according to an embodiment of the invention includes: a first step of culturing a pluripotent stem cell in a presence of a ROCK inhibitor during a first time period; a second step of culturing the pluripotent stem cell, which has been subjected to the first step, without the ROCK inhibitor during a second time period following the first time period; and a step of culturing the pluripotent stem cell, which has been subjected to the second step, in the presence of the ROCK inhibitor during a third time period following the second time period, in which the pluripotent stem cell is cultured in a state of being adhered to the cell culture substrate including the planar mesh through the first to third time periods. FIG. 1 schematically shows the method of culturing the pluripotent stem cells of the invention. By culturing the pluripotent stem cells by this method, differentiation into trophoblast can be induced.

The pluripotent stem cells used herein are not particularly limited, but are preferably human pluripotent stem cells. The pluripotent stem cells refer to cells that can be cultured in vitro and can differentiate into almost all cells that make up a living body. Specifically, examples of the pluripotent stem cells include: induced pluripotent stem cells (iPS cells), embryonic stem cells (ES cells), embryonic germ cells (EG cells), germline stem cells (GS cells), embryonic carcinoma cells (EC cells), and nuclear transfer embryonic stem cells (ntES cells), but the iPS cells and the ES cells are preferable, and the iPS cells are more preferable.

The cell culture substrate may be coated with a material serving as a scaffold for adherent cells as a pretreatment for use in the cell culturing, in order to settle the cells on the planar mesh 1 and facilitate spreading and proliferation. Examples of the material serving as the scaffold include, but are not limited to, an extracellular matrix protein such as collagen, fibronectin, and laminin and a fragment thereof, and a positively charged substance such as poly-L-lysine. For coating, for example, in a case of i-Matrix (Nippi Inc.), a solution having a concentration of 50 ng/µl can be used, and a concentration, a treatment temperature and a treatment time can be appropriately adjusted by those skilled in the art.

The ROCK inhibitor is not limited to a specific compound, and can be appropriately selected from substances having a ROCK inhibitory effect. As an example, Y-27632 is exemplified as a compound having the ROCK inhibitory effect.

In a step of seeding the pluripotent stem cells on the cell culture substrate, the cells are adhered to the cell culture substrate by adding a cell suspension in which single cells are dispersed on the cell culture substrate. The step can be carried out as appropriate by a known method or a modified method thereof. For example, the cells maybe suspended in a medium and dropped onto the cell culture substrate by a pipette or the like. Any medium may be used as the medium required for the step as long as it is recommended for each cell, and the number of cells may be appropriately adjusted in consideration of a culture area. After the cells are seeded on the cell culture substrate, the cell culture substrate is placed in the cell culture container in a state of being suspended in the medium. By placing the cell culture substrate in a state of being suspended in the medium, culture conditions appropriate for the cells can be maintained since all the cells can take in required nutrients from the medium and discharge unwanted substances. Since dead cells and degraded cells naturally fall off from the cell culture substrate, the cells can be cultured on the cell culture substrate for a long time period without cell passaging.

In the first time period, cell death of the pluripotent stem cells is prevented by culturing the cells in the medium containing the ROCK inhibitor (hereinafter referred to as ROCK inhibitor-containing medium). The first time period is a time period from a start of culturing to Day 1 after the start of culturing. In the present specification, Day n means (n×24 hours±12 hours), that is, (n days±0.5 days). For example, in a case of performing culturing from the start of culturing to Day 1 after the start of culturing, the culturing may be performed within 12 hours to 36 hours after the start of culturing. The ROCK inhibitor-containing medium can be prepared by adding the ROCK inhibitor to a liquid medium (for example, Essential 8, DMEM, HAM 12, RPMI 1640) generally used for the cell culturing. An amount of the ROCK inhibitor added in this step is not particularly limited, but as a final concentration, 1 $\mu$M to 100 $\mu$M is preferable, 2 $\mu$M to 50 $\mu$M is more preferable, 3 $\mu$M to 30 $\mu$M is further more preferable, and 10 $\mu$M is even more preferable.

In the second time period, the pluripotent stem cells cultured in the ROCK inhibitor-containing medium in the first time period are cultured in a medium containing no ROCK inhibitor (hereinafter, referred to as ROCK inhibitor-free medium). The second time period is a time period from Day 1 after the start of culturing to Day 7 to Day 15 after the start of culturing. For example, after the start of culturing, from Day 1 to Day 7, from Day 1 to Day 9, from Day 1 to Day 11, from Day 1 to Day 13, or from Day 1 to Day 15, the pluripotent stem cells are cultured in the ROCK inhibitor-free medium. Preferably, the second time period is a time period from Day 1 after the start of culturing to Day 9 to Day 13 after the start of culturing. As described above, since Day n means (n days±0.5 days), for example, "the second time period is from Day 1 after the start of culturing to Day 7 after the start of culturing" means that the culturing in the ROCK inhibitor-free medium is started between 12 hours and 36 hours after the start of culturing, and the culturing in the ROCK inhibitor-free medium is completed between 6.5 days and 7.5 days after the start of culturing. In general, as the ROCK inhibitor-free medium, the liquid medium (for example, Essential 8, DMEM, HAM 12, RPMI 1640) used for the cell culturing may be used without adding the ROCK inhibitor. A basic medium may be the same as or different from the ROCK inhibitor-containing medium, and an operator can appropriately select the medium.

In the third time period, induction of differentiation into trophoblast is promoted by culturing the pluripotent stem cells again in the ROCK inhibitor-containing medium. The third time period is a time period from Day 7 to Day 15 after the start of culturing to Day 11 or later after the start of culturing. If an end of the third time period is Day 11 or later, the pluripotent stem cells can be cultured in the ROCK inhibitor-containing medium until an end of the culturing. For example, after the start of culturing, from Day 7 to Day 11, from Day 7 to Day 13, from Day 7 to Day 17, from Day 7 to Day 21, from Day 9 to Day 11, from Day 9 to Day 13, from Day 9 to Day 17, from Day 9 to Day 21, from Day 13 to Day 17, from Day 13 to Day 21, from Day 15 to Day 17, and from Day 15 to Day 21, the pluripotent stem cells may be cultured in the ROCK inhibitor-containing medium. Preferably, the third time period is a time period from Day 9 to Day 13 after the start of culturing to Day 13 to Day 21 after the start of culturing. "The third time period is from Day 9 after the start of culturing to Day 21 after the start of culturing" means that the culturing in the ROCK inhibitor-containing medium is started between 8.5 days and 9.5 days after the start of culturing, and the culturing in the ROCK inhibitor-containing medium is completed between 20.5 days and 21.5 days after the start of culturing. The third time period is not only defined by the number of days, but may also be started when the cells start to form a cyst structure. The ROCK inhibitor-containing medium can be prepared generally by adding the ROCK inhibitor to the medium used for the cell culturing. The amount of the ROCK inhibitor added in this step is not particularly limited, but as a final concentration, 1 $\mu$M to 200 $\mu$M is preferable, 2 $\mu$M to 100 $\mu$M is more preferable, 3 $\mu$M to 60 $\mu$M is further more preferable, and 20 $\mu$M is even more preferable.

The cell culture container containing the cell culture substrate is placed in an environment suitable for culturing and the medium is periodically replaced with a new medium. Half of the medium may be replaced at once, or all of the medium may be replaced. The medium used for culturing, a culture environment (temperature and carbon dioxide concentration), and a timing of medium replacement may be performed under known conditions recommended for the cells to be used.

5. Cell Culture Apparatus

The automatic cell culture apparatus of the invention may automatically perform the cell culture method as described above. For example, the automatic cell culture apparatus includes a mechanism for automatically or partially manually performing a step of seeding the cells, a step of incubating the cells, a step of replacing the medium, a step of observing the cells, and a step of analyzing an observation image.

Figure 4:
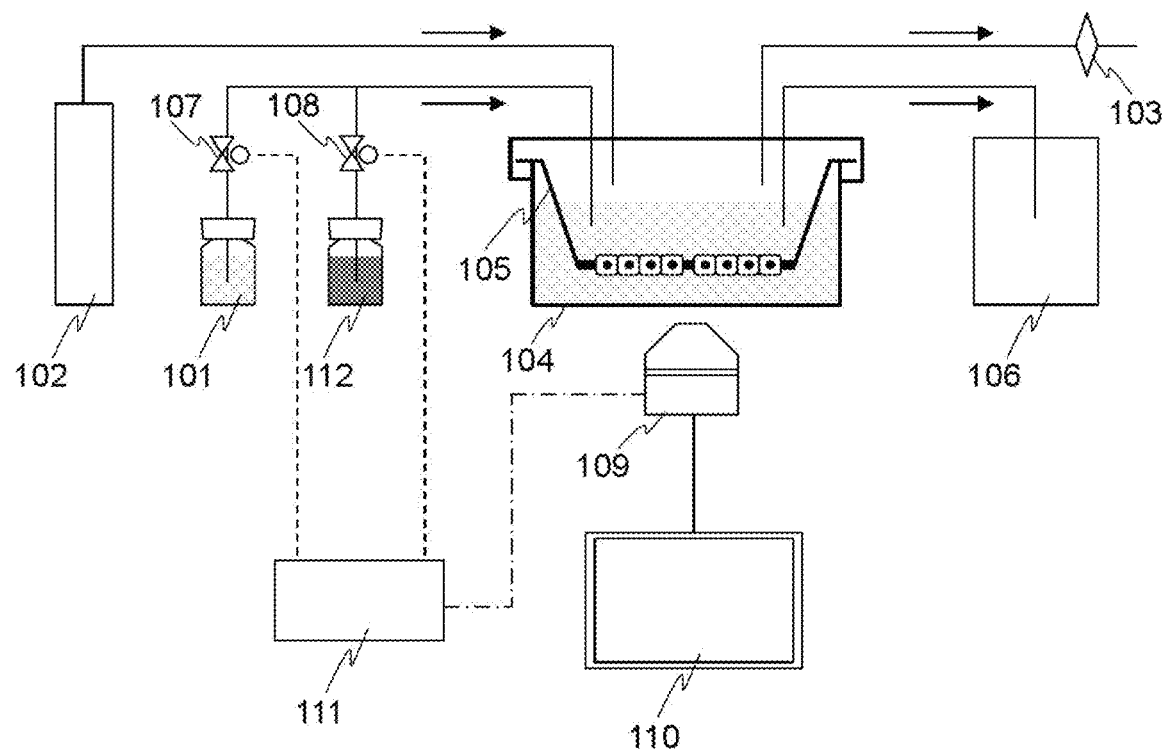
FIG. 4 is a schematic view of a cell culture apparatus having a cell observation mechanism and a cell culture medium switching mechanism according to the embodiment of the invention.

In one embodiment of the cell culture apparatus, a method of culturing cells using a closed automatic culture apparatus 100 shown in FIG. 4 will be described below. First, after a cell culture substrate 105 is placed in a closed cell culture container 104, target cells are seeded on the cell culture substrate 105, or after the target cells are seeded on the cell culture substrate 105, the cell culture substrate 105 is placed in the closed cell culture container 104 so as to prepare the closed cell culture container 104 having the cell culture substrate 105 to which the cells are attached. Next, a fixed amount of ROCK inhibitor-free medium is supplied from a cell culture medium tank 101 and incubated for a certain period of time. During this time, a carbon dioxide concentration adjusting mechanism 102 keeps a partial pressure of carbon dioxide in the closed cell culture container 104 constant. In order to keep the partial pressure constant, a gas in the apparatus is appropriately discharged to an outside of the apparatus through a filter 103. Thereafter, at a time of replacing the medium, the medium during the culturing is discharged from the closed cell culture container 104 to a waste liquid tank 106, and a fixed amount of a new ROCK inhibitor-free medium is supplied from the cell culture medium tank 101 to the closed cell culture container 104, so that the cells are maintained.

At a start of the method of the invention, a first valve 107 is closed, a second valve 108 is opened, and a supply source of the medium is switched from the cell culture medium tank 101 that supplies the ROCK inhibitor-free medium to a cell culture medium tank 112 that supplies the ROCK inhibitor-containing medium, so that the medium is replaced, and the culturing is performed for the first time period. During this time, the medium is replaced with the medium in the cell culture medium tank 112 as appropriate. After the first time period is completed, the second valve 108 is closed, the first valve 107 is opened, and the supply source of the medium is switched from the cell culture medium tank 112 that supplies the ROCK inhibitor-containing medium to the cell culture medium tank 101 that supplies the ROCK inhibitor-free medium, so that the medium is replaced, and the culturing is performed for the second time period. During this time, the medium is replaced with the medium in the cell culture medium tank 101 as appropriate. After the second time period is completed, the first valve 107 is closed, the second valve 108 is opened, and the supply source of the medium is switched from the cell culture medium tank 101 that supplies the ROCK inhibitor-free medium to the cell culture medium tank 112 that supplies the ROCK inhibitor-containing medium, so that the medium is replaced, and the culturing is performed for the third time period. During this time, the medium is replaced with the medium in the cell culture medium tank 112 as appropriate. When the third time period is completed, the culturing is ended.

Through a culture time period, an observation mechanism 109 can acquire an image of the mesh on the plane inside the closed cell culture container 104. Based on the acquired image, it may be determined whether the cyst structure is generated above and below the planar mesh. This determination may be automatically determined by a control mechanism 111 or may be determined by an observer.

The embodiment of the invention also provides a program for executing such a method and a computer-readable storage medium in which the program is stored.

EXAMPLE

First Example

In the present example, human iPS cells (201B7 strain) were cultured by using a culture substrate in which a planar mesh made of nickel was coated with parylene or Au.

First, a rhombus planar mesh made of pure nickel was prepared by an electroforming method so that a length of a side was 100 μm and a wire diameter of a mesh wire was 5 μm. Parylene was deposited on a surface of the mesh to have a thickness of 500 nm and Au was deposited to have a thickness of 50 nm. An end of the prepared mesh was affixed to a silicon plate (Tigers Polymer Co.) using a Kapton (registered trademark) tape to prepare a cell culture substrate. The cell culture substrate was sterilized by irradiation with a UV lamp for 12 hours or more, and then placed in a cell culture container. Next, i-Matrix (Nippi Inc.) adjusted to a concentration of 50 ng/μl as a scaffold material was added so as to cover the mesh and the mixture was treated at 4° C. for 3 days. After that, i-Matrix was removed and the washing was performed with an Essential 8 medium (GIBCO Co.).

Next, the human iPS cells (201B7 strain) was adjusted in the Essential 8 medium so as to be $1\times10^5$/ml, and an iPS cell suspension containing 10 μM of ROCK inhibitor (Y-27632, Wako Pure Chemical Co.) was added on the mesh in the same manner as the scaffold material, and the cells were incubated at 37° C. in the cell culture apparatus adjusted to a $CO_2$ concentration of 5%. After 24 hours from seeding, a total amount of iPS cell suspension was removed and replaced with a new Essential 8 medium. Then, every 4 days, half the amount of the medium was removed, and the amount of the medium was maintained by adding a new Essential 8 medium in an amount equal to a removed amount. Culturing was carried out for 3 weeks, and follow-up observation was performed with a phase contrast microscope.

Figure 5:
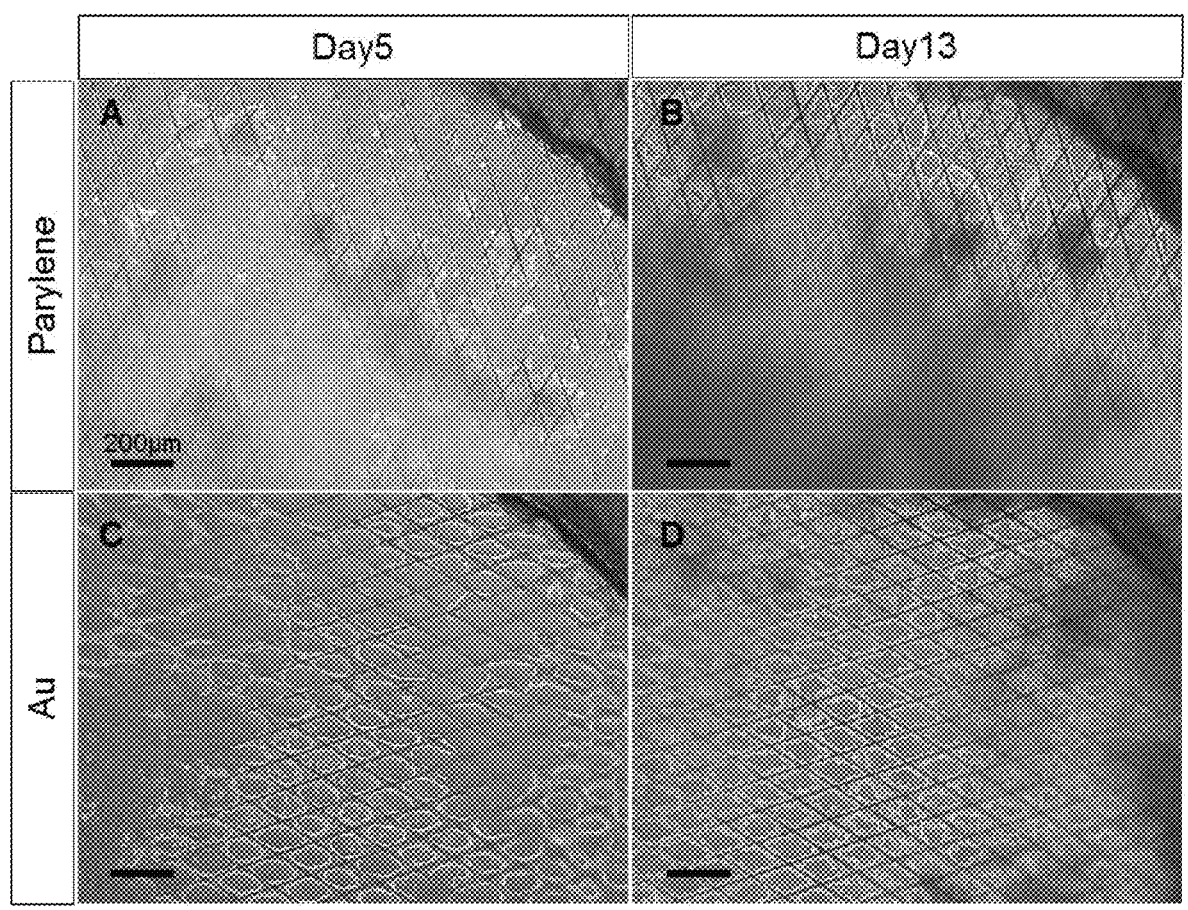
FIG. 5 shows bright-field microscopic images on Day 5 of culturing (image A, image C) and Day 13 of culturing (image B, image D) when a 201B7 strain is cultured on a rhombus mesh treated with parylene coating (image A, image B) and Au coating (image C, image D) in a first example of the invention.

FIG. 5 shows a picture acquired by the phase contrast microscope. When the mesh was coated with Au, it was confirmed by observation on Day 5 of the culturing that the cells showed a planar proliferation along the mesh wire, but when the mesh was coated with parylene, it was observed that a part of the cells were aggregated on the mesh wire. On the other hand, when observed on Day 13 of the culturing, no significant difference was observed in a cell adhesion mode regardless of whether the mesh was coated with parylene or Au, and cells adhered and proliferated along the mesh wire.

As described above, the iPS cells can be cultured in the cell culture substrate using either Au or parylene as a coating agent of the mesh.

Second Example

In the present example, the human iPS cells (201B7 strain) were cultured by using a culture substrate in which the planar mesh made of nickel was coated with parylene or Au, and an effect of the ROCK inhibitor on cell differentiation was investigated.

The 201B7 strain (Zhuosi Li et al., Stem Cell Research & Therapy, 2019), which is a cell line that does not form a cyst structure and does not differentiate into trophoblast when cultured on a mesh in the related art, was used.

A cell culture substrate was prepared in the same procedure as in the first example. The i-Matrix (Nippi Inc.) adjusted to a concentration of 50 ng/μl as a scaffold material of cells was added so as to cover the mesh and the mixture was treated at 4° C. for 3 days. Thereafter, after i-Matrix was removed, and the washing was performed with an Essential 8 medium (GIBCO Co.), the human iPS cells (201B7 strain) was adjusted in the Essential 8 medium so as to be $1\times10^5$/ml, and an iPS cell suspension containing 10 μM of the ROCK inhibitor (Y-27632, Wako Pure Chemical Co.) was added on the mesh in the same manner as the scaffold material, and the cells were incubated at 37° C. in the cell culture apparatus adjusted to the $CO_2$ concentration of 5%.

After 24 hours from seeding, a total amount of iPS cell suspension was removed and replaced with a new Essential 8 medium, so that the ROCK inhibitor was completely removed once. Then, every 4 days, half the amount of culture supernatant was recovered, and the amount of culture supernatant was maintained by adding a new Essential 8 medium in an amount equal to a removed amount. The ROCK inhibitor (Y-27632, Wako Pure Chemical Co.) was added to a part of the medium of the cell culture substrate on which the 201B7 strain is seeded from Day 9 of culturing or Day 13 of the culturing so that the final concentration of the ROCK inhibitor was 20 μM, and the culturing was performed for 3 weeks.

A secretion amount of hCG, which is one of trophoblast differentiation markers, was quantified by using the recovered culture supernatant. For the quantification, a value of $OD_{450}$ was detected with an absorbance plate reader (Corona Electric Co. Ltd.) by using a Human hCG ELISA Kit (Abcam Co.). Details of an ELISA reaction and a measurement method followed a manual of a kit.

FIG. 6 shows the secretion amount of hCG when the 201B7 strain was cultured on the mesh coated with parylene. When the ROCK inhibitor was added from Day 9 of the culturing, the secretion amount of hCG was increased to about twice on Day 13 of the culturing as compared with a case where the ROCK inhibitor was not added, and the secretion amount was maintained thereafter. When the ROCK inhibitor was added from Day 13 of the culturing, the secretion amount of hCG was increased to about twice on Day 17 of the culturing as compared with the case where the ROCK inhibitor was not added, and was increased to about three times on Day 21 of the culturing.

FIG. 7 shows the secretion amount of hCG when the 201B7 strain was cultured on the mesh coated with Au. When the mesh was coated with Au, a time when secretion of hCG was started tended to be slightly delayed as compared with a case where the mesh was coated with parylene. On the other hand, when the ROCK inhibitor was added from Day 9 of the culturing, the secretion amount was increased to about twice on Day 17 of the culturing as compared with the case where the ROCK inhibitor was not added, and increased to four times or more on Day 21 of the culturing. When the ROCK inhibitor was added from Day 13 of the culturing, the secretion amount was increased to about three times on Day 17 of the culturing as compared with the case where the ROCK inhibitor was not added, and the secretion amount was maintained thereafter.

From the above, it was shown that when the 201B7 strain is cultured on the planar mesh coated with parylene or Au, the differentiation into trophoblast is promoted by re-addition of the ROCK inhibitor.

Third Example

In the present example, a 253G1 strain (Zhuosi Li et al., Stem Cell Research & Therapy, 2019), which is a cell line that does not form a cyst structure and does not differentiate into trophoblast when cultured on a mesh in the related art, was used, and an effect of the ROCK inhibitor on the cell differentiation was investigated.

Preparation of the cell culture substrate and seeding of the iPS cells were carried out in the same manner as in the second example. After 24 hours from seeding, a total amount of iPS cell suspension was removed and replaced with a new Essential 8 medium, so that the ROCK inhibitor was completely removed once. Then, every 4 days, half the amount of the culture supernatant was recovered, and the amount of culture supernatant was maintained by adding a new Essential 8 medium in an amount equal to a removed amount. The ROCK inhibitor (Y-27632, Wako Pure Chemical Co.) was added to a part of the medium of the cell culture substrate on which the 253G1 strain is seeded from Day 9 of culturing or Day 13 of the culturing so that a final concentration was 20 µM, and the culturing was performed for 3 weeks.

The secretion amount of hCG, which is one of trophoblast differentiation markers, was quantified by using the recovered culture supernatant. For the quantification, the value of $OD_{450}$ was detected by an absorbance plate reader (Corona Electric Co.) by using a Human hCG ELISA Kit (Abcam Co.). Details of an ELISA reaction and a measurement method followed a manual of a kit.

Figure 8:
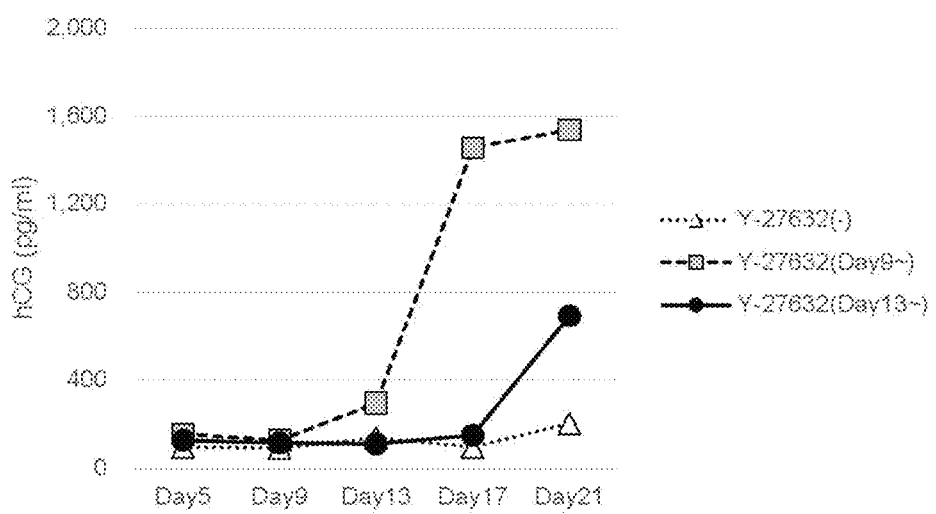
FIG. 8 is a graph showing an amount of hCG secreted into culture supernatant when a 253G1 strain is cultured on a rhombus mesh treated with parylene coating in a third example of the invention.

FIG. 8 shows the secretion amount of hCG when the 253G1 strain was cultured on the mesh coated with parylene. For the 253G1 strain, unlike the 201B7 strain, almost no secretion of hCG was observed when the ROCK inhibitor was not added. On the other hand, when the ROCK inhibitor was added from Day 9 of the culturing, the secretion amount of hCG was increased to about ten times on Day 17 of the culturing as compared with the case where the ROCK inhibitor was not added, and the secretion amount was maintained thereafter. In addition, when the ROCK inhibitor was added from Day 13 of the culturing, the secretion amount of hCG was increased to three times or more on Day 21 of the culturing as compared with the case where the ROCK inhibitor was not added.

Figure 9:
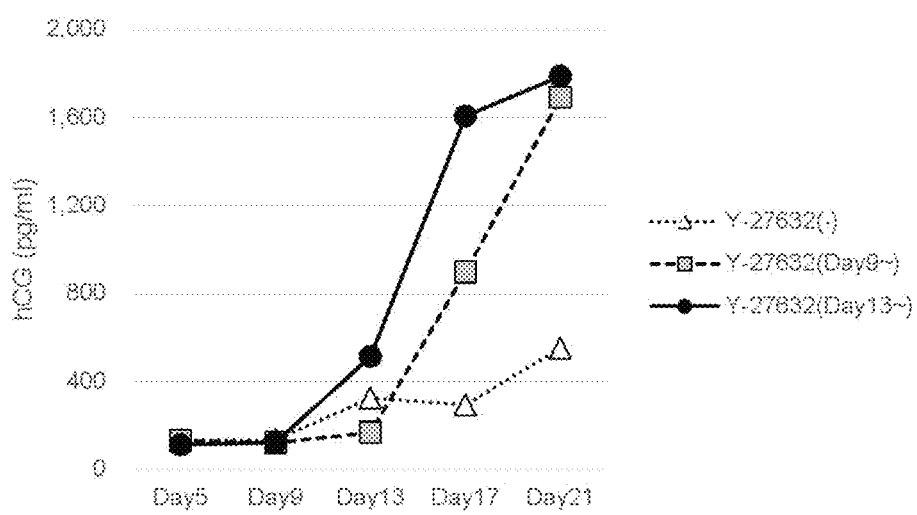
FIG. 9 is a graph showing an amount of hCG secreted into the culture supernatant when the 253G1 strain is cultured on the rhombus mesh treated with Au coating in the third example of the invention.

FIG. 9 shows the secretion amount of hCG when the 253G1 strain was cultured on the mesh coated with Au. When the mesh was coated with Au, as in a case of parylene, almost no secretion of hCG was observed when the ROCK inhibitor was not added. On the other hand, when the ROCK inhibitor was added from Day 9 of the culturing, the secretion amount of hCG was increased to about twice on Day 17 of the culturing as compared with the case where the ROCK inhibitor was not added, and was increased to about three times on Day 21 of the culturing. When the ROCK inhibitor was added from Day 13 of the culturing, the secretion amount of hCG was increased to five times or more on Day 17 of the culturing as compared with the case where the ROCK inhibitor was not added, and the secretion amount was maintained thereafter.

From the above, it was shown that when the 253G1 strain is cultured on the planar mesh coated with parylene or Au, the differentiation into trophoblast cells is promoted by addition of the ROCK inhibitor.

What is claimed is:

1. A cell culture method for inducing differentiation of a pluripotent stem cell into a trophoblast, the cell culture method comprising:
   a first step of seeding the pluripotent stem cell on a cell culture substrate including a planar mesh made of a first metal and coated with at least one of Au or parylene, and culturing the pluripotent stem cell adhered to the cell culture substrate in a presence of a ROCK inhibitor at a concentration of 1 µM to 100 µM during a first time period from a start of culturing to Day 1 after the start of culturing;
   a second step of culturing the cell adhered to the cell culture substrate, which has been subjected to the first step, without the ROCK inhibitor during a second time period extending from an end of the first time period to a time that is from 9 to 13 days after the start of the culturing; and
   a third step of culturing the cell adhered to the cell culture substrate, which has been subjected to the second step, in the presence of the ROCK inhibitor at a concentration of 1 µM to 200 µM during a third time period extending from an end of the second time period to a time that is from 4 to 12 days after the end of the second time period, wherein
   the pluripotent stem cell has differentiated into the trophoblast during at least one of the second step or the third step.

2. The cell culture method according to claim 1, wherein Day 1 after the start of culturing comprises a time from 12 to 36 hours after the start of culturing.

3. The cell culture method according to claim 1, wherein the first metal is nickel,
   the parylene is a first coating on the planar mesh, and
   the first coating is coated with a film containing the Au.

4. The cell culture method according to claim 3, wherein the planar mesh comprises wires of a first thickness of 5 µm,
   the first coating has a thickness of 0.5 µm, and
   the film has a thickness of 0.05 µm.

5. The cell culture method according to claim 1, wherein the pluripotent stem cell is adhered to the cell culture substrate continuously throughout the first step, the second step, and the third step.

6. The cell culture method according to claim 1, wherein
the ROCK inhibitor is present at a first concentration during the first time period, and
the ROCK inhibitor is present at a second concentration that is greater than the first concentration during the third time period.

7. The cell culture method according to claim 6, wherein
the first concentration is 10 μM, and
the second concentration is 20 μM.

8. The cell culture method according to claim 1, wherein the second time period is a time period from Day 1 after the start of culturing to Day 9 after the start of culturing, and
the third time period is a time period from Day 9 to any of Day 13 to Day 21 after the start of culturing.

* * * * *